(12) United States Patent
Ho et al.

(10) Patent No.: US 8,858,972 B2
(45) Date of Patent: *Oct. 14, 2014

(54) ANTIMICROBIAL MEDICOTECHNICAL PRODUCT, PROCESS FOR ITS PREPARATION AND USE

(75) Inventors: Chau Hon Ho, Freiburg (DE); Erich K. Odermatt, Schaffhausen (CH); Rainer Bargon, Mengen (DE); Jörg Tiller, Freiburg (DE)

(73) Assignee: Aesculap AG, Tuttlingen/Donau (DE)

( * ) Notice: Subject to any disclaimer, the term of this patent is extended or adjusted under 35 U.S.C. 154(b) by 1566 days.

This patent is subject to a terminal disclaimer.

(21) Appl. No.: 11/662,171

(22) PCT Filed: Sep. 7, 2006

(86) PCT No.: PCT/EP2006/008714

§ 371 (c)(1),
(2), (4) Date: Apr. 8, 2008

(87) PCT Pub. No.: WO2007/028607

PCT Pub. Date: Mar. 15, 2007

(65) Prior Publication Data

US 2008/0292671 A1    Nov. 27, 2008

(30) Foreign Application Priority Data

Sep. 9, 2005  (DE) .......................... 10 2005 044 360
Mar. 3, 2006  (DE) .......................... 10 2006 011 217

(51) Int. Cl.

| A61K 47/00 | (2006.01) |
| A01N 25/00 | (2006.01) |
| A61L 31/08 | (2006.01) |
| A61L 27/34 | (2006.01) |
| A61L 31/16 | (2006.01) |
| A61L 27/54 | (2006.01) |
| A61L 31/10 | (2006.01) |
| A61L 27/30 | (2006.01) |

(52) U.S. Cl.
CPC ............ *A61L 31/10* (2013.01); *A61L 2300/214* (2013.01); *A61L 31/082* (2013.01); *A61L 2300/404* (2013.01); *A61L 27/34* (2013.01); *A61L 31/16* (2013.01); *A61L 27/54* (2013.01); *A61L 2400/12* (2013.01); *A61L 2300/102* (2013.01); *A61L 27/30* (2013.01)
USPC ........................ 424/405; 514/772.1; 514/773

(58) Field of Classification Search
None
See application file for complete search history.

(56) References Cited

U.S. PATENT DOCUMENTS

| 6,616,946 | B1 * | 9/2003 | Meier et al. ................... 424/489 |
| 8,105,619 | B2 * | 1/2012 | Odermatt et al. ............. 424/405 |
| 2003/0224974 | A1 * | 12/2003 | Bolotin ............................ 514/6 |
| 2004/0087730 | A1 * | 5/2004 | Harada et al. .............. 525/329.7 |
| 2004/0171978 | A1 | 9/2004 | Shalaby |
| 2004/0234604 | A1 | 11/2004 | Mecking et al. |
| 2005/0058844 | A1 * | 3/2005 | Rubner et al. ................. 428/457 |
| 2005/0070721 | A1 * | 3/2005 | Bae et al. ................... 548/339.1 |
| 2005/0130240 | A1 | 6/2005 | Lin et al. |
| 2006/0041058 | A1 * | 2/2006 | Yin et al. ........................ 525/50 |

FOREIGN PATENT DOCUMENTS

| CN | 1456356 | 11/2003 |
| DE | 103 23 597 | 12/2004 |
| WO | 98/50461 | 11/1998 |
| WO | 03/072143 | 9/2003 |
| WO | 2004/056403 | 7/2004 |
| WO | 2004/056404 | 7/2004 |
| WO | 2004/056407 | 7/2004 |
| WO | 2004/085998 | 10/2004 |
| WO | 2004/101011 | 11/2004 |
| WO | 2007/028607 | 3/2007 |

OTHER PUBLICATIONS

Wikipedia "polyethyleneimine" retrieved online on Jan. 25, 2012 (pp. 1-2).*
Vancha et al "Use of polyethyleneimine polymer in cell culture as attachment factor and lipofection enhancer" BMC Biotechnology, Oct. 15, 2004, 4:23 (12 pages).*
Aymonier et al., "Hybrids of Silver Nanoparticles with Amphiphilic Hyperbranched Macromolecules Exhibiting Antimicrobial Properties." *Chem. Commun.*, pp. 3018-3019, 2002.

* cited by examiner

*Primary Examiner* — Bethany Barham
(74) *Attorney, Agent, or Firm* — Nath, Goldberg & Meyer; Tanya E. Harkins

(57) ABSTRACT

The invention relates to a medicotechnical product having an antimicrobial finish of a complex material of metal nanoparticles and macromolecules, the macromolecules being formed at least partially from a polyamino acid.

32 Claims, No Drawings

ANTIMICROBIAL MEDICOTECHNICAL PRODUCT, PROCESS FOR ITS PREPARATION AND USE

The invention relates to a medicotechnical product having an antimicrobial finish, to a process for its preparation and to the use of the antimicrobial finish as a biocide in medicotechnical products.

The permanently increasing demands on hygienic standards in recent years are leading, in particular in the field of medicine, to a considerable need for antimicrobial materials. Since common consumables, for example wood, ceramic, plastic, glass or steel have no antimicrobial properties themselves, they must be rendered antimicrobial.

A highly efficient approach is based on "contact-active" systems, where materials are provided with an antimicrobial modification such that microorganisms are killed on contact with the modified material without, in contrast to the release systems which are just as common, releasing an antimicrobial compound which is only present in limited amount. Contact-active systems often consist of grafted antimicrobial polymers, in particular polycationic polymers having ammonium, pyridinium, biguanidine, sulfonium or phosphonium groups. However, the application of the polymers to the material concerned not rarely necessitates complicated surface modifications. Thus it is known, for example, from US 2004/0171978 A1 that for the immobilization of polylysine on a polymer surface, a sulfonation of the surface is first carried out. Moreover, a few contact-active systems are only restrictedly employable for medical applications on account of toxic properties of some antimicrobial polymers.

In the medical and clinical field, however, there are high demands on the biocompatibility of materials, in particular on those which are intended for surgical use. Frequently, there therefore remains only a small margin between antimicrobial activity and biocompatibility of the material concerned.

The object of the present invention is therefore to make available medicotechnical products having high antimicrobial activity on the one hand and high biocompatibility on the other hand.

This object is achieved by a medicotechnical product having an antimicrobial or biocidal finish of a complex material of metal nanoparticles and macromolecules, the macromolecules being formed at least partially from a polyamino acid.

An antimicrobial or biocidal finish in the sense of the present invention should be understood as meaning a finish which prevents cell growth and/or proliferation of microorganisms, in particular of germs (harmful microorganisms), and/or causes the destruction of microorganism colonies present, in particular germ colonies.

According to one embodiment of the medicotechnical product, the antimicrobial finish is provided on at least one part of the surface of the product, in particular in the form of a coating. The antimicrobial finish is preferably present on at least one part of the surface of the product, in particular in the form of a coating. Preferably, the antimicrobial finish extends over the entire surface of the medicotechnical product. The medicotechnical product finished in this way is advantageously distinguished in that an adequately stable adhesive connection between the finish and the surface of the product material exists, such that, for example, removal, in particular wiping off or washing off, of the finish from the coated product is prevented and thus a medium-term, long-term and effective prevention against microbial colonization of the medicotechnical product, in particular after application has taken place, is guaranteed. The adhesive connection can be based on electrostatic attractive forces, hydrogen bridges and/or lipophilic interactions, in particular van der Waals forces.

Additionally or alternatively to the embodiment just described, it can be provided according to the invention for the complex material to be situated within the product. This can be particularly advantageous if the material of the medicotechnical product is a polymer or alternatively another material whose preparation process permits the introduction of the complex material into the interior of the product. In this way, a uniformly distributed antimicrobial activity of the medicotechnical product can be achieved.

In a further embodiment, each metal nanoparticle is surrounded by at least one polyamino acid, each metal nanoparticle preferably being surrounded on all sides in a shell-like manner by at least one polyamino acid. Preferably, the polar, in particular charged, part of the polyamino acid is oriented toward the metal nanoparticles and makes possible by means of the heteroatoms or heteroatom groups situated in the polar part, for example nitrogen and/or oxygen atoms, coordinative or donative bonds to the metal nanoparticles. According to the invention, the metal nanoparticles can be partially positively polarized in this way.

The polyamino acid can in particular be a homo- or heteropolyamino acid, a homopolyamino acid being particularly preferred. The polyamino acid can consist of naturally occurring and/or synthetic amino acids, naturally occurring amino acids, in particular α-aminocarboxylic acids, in particular α-aminocarboxylic acids having an L configuration, being preferred. Preferably, the amino acids are at least trifunctional amino acids. A trifunctional-amino acid in the sense of the present invention should be understood as meaning an amino acid which contains, in addition to the carboxyl and α-amino group, a further organic functional group, in particular a further hydroxyl, thiol, guanidine or amino group, preferably a further amino group. Preferably, the polyamino acid contains at least one amino acid carrying a basic, acidic and/or sulfur-containing group. The sulfur-containing group can in particular be thiol and/or thioether groups. Particularly preferably, the polyamino acid contains at least one amino acid from the group comprising cysteine, methionine, tryptophan, histidine, arginine, lysine, ornithine, aspartic acid, glutamic acid and their derivatives.

Advantageously, the polyamino acid has a linear structure. The linear structure permits a tightly packed arrangement around the metal nanoparticles to be stabilized, the arrangement being stabilized in particular by electrostatic forces, hydrogen bridges and/or lipophilic interactions, in particular van der Waals forces.

In another preferred embodiment of the invention, the polyamino acid has a branched, preferably a hyperbranched, structure. The branched structure in particular permits a compact arrangement around the metal nanoparticles to be stabilized, by means of which, in particular, the stabilization of the metal nanoparticles is increased. Furthermore, the branched structure of the polyamino acid advantageously causes a decreased brittleness of the complex material of the product according to the invention. Branched polyamino acids thus preferably increase the film-forming properties of the complex material.

According to a preferred embodiment of the medicotechnical product, the polyamino acid is polylysine, in particular poly-α-lysine (poly-alpha-lysine) and/or poly-ε-lysine (poly-epsilon-lysine). Both poly-α-lysine and poly-ε-lysine have antimicrobial properties, poly-ε-lysine being more biocompatible in contrast to poly-α-lysine and therefore being particularly preferred. The polylysine of the product according to the invention in particular has a degree of polymerization (DP) of 10 to 15, in particular 12 to 14, preferably of about 13. The molecular weight of the polylysine is preferably between 3000 g/mol and 6000 g/mol, in particular between 4000 g/mol and 5000 g/mol.

According to a preferred embodiment of the medicotechnical product, the polyamino acid is amphiphilically modified with a substance, in particular with such a substance having at least one aliphatic radical. A modification of this type can be particularly preferred in order to increase the stabilization of the metal nanoparticles and the mutual screening of the polyamino acids coordinating the nanoparticles. In this way, the formation of larger nanoparticles, in particular in the form of aggregates, can be prevented. Furthermore, the formation of aggregates of polyamino acids can be avoided. Preferably, the aliphatic radical is oriented outward after modification of the polyamino acid, in particular away from the metal nanoparticles. The structure of metal nanoparticles and amphiphilically modified polyamino acids thus obtained can be described as a "core-shell structure" (core-shell particle), the polyamino acids immediately surrounding the metal nanoparticles representing the core and the substance representing the shell of the structure. Amphiphilicity in the sense of the present invention should be understood as meaning the property of a compound which, on account of its molecular structure, has both hydrophilic and lipophilic properties. A complex having a core-shell structure is known, in particular, from DE 103 23 597 A1, which consists essentially of amphiphilically modified polyethyleneimine.

Preferably, the aliphatic radical of the substance has 6 to 22, in particular 12 to 18, preferably 16 and/or 18, carbon atoms. The aliphatic radical can be an alkyl, alkenyl and/or an alkynyl substituent, alkyl substituents, in particular unbranched alkyl substituents, being particularly preferred. Thus, alkyl substituents, in particular long-chain and preferably unbranched alkyl substituents, permit a tighter or more compact alignment of the alkyl chains to one another in the region of the shell of the core-shell structure, which is essentially based on lipophilic interactions, in particular on van der Waals forces.

Preferably, the substance is at least one biocompatible substance, in particular a fatty acid or a fatty acid derivative, preferably palmitic and/or stearic acid. For the amphiphilic modification of the polyamino acid, it can be preferred for the fatty acid to be present as a fatty acid derivative, in particular in an activated form, preferably as a fatty acid chloride. Furthermore, it can be preferred according to the invention for the substance to be present as a mixture of various substances, in particular various fatty acids or fatty acid derivatives. Thus, in particular a mixture of palmitoyl and stearoyl chloride, for example a mixture of 60 parts by weight of stearoyl chloride and 40 parts by weight of palmitoyl chloride is particularly preferred because of its lower price in comparison to the pure fatty acid chlorides.

According to a particularly preferred embodiment of the product according to the invention, the amphiphilic modification of the polyamino acid with the substance is based on covalent bonds, in particular on amide bonds. Preferably, the amide bonds are formed from the free amino groups of the polyamino acid and acyl groups of the substance. In the case of poly-ε-lysine, the free amino groups are the α-amino groups of the polyamino acid. Starting from the pure lysine monomers, the content of free amino groups after preparation of the unmodified polyamino acid is usually about 50%. The medicotechnical product is preferably distinguished in that the content of free amino groups of the polyamino acid after the amphiphilic modification of the polyamino acid is between 0.5 and less than 50%, in particular between 10 and 40%, in particular between 20 and 40%, preferably about 37%, based on the original total amount of amino groups of the amino acid monomers, preferably lysine monomers, used for the preparation of the polyamino acid.

According to a further particularly preferred embodiment of the medicotechnical product, the substance is bonded to the polyamino acid by means of a crosslinking component, in particular a polyfunctional carboxylic acid, preferably citric acid. The crosslinking is preferably based on the formation of covalent bonds, in particular amide bonds, the amide bonds being formed by condensation between the amino groups of the polyamino acid and acid groups, in particular carboxyl groups, of the crosslinking component. The crosslinking of the polyamino acid is particularly advantageous, since in this manner, after the amphiphilic modification of the crosslinked polyamino acid closed core-shell structures are present, and the functional groups, in particular carboxyl groups, of the crosslinking component increase the number of possible coordination sites for the metal nanoparticles in the polymer. In this way, the complexing properties for the metal nanoparticles can be improved. Furthermore, certain properties of the biocidal complex material, in particular its film-forming properties, can be improved by the crosslinking.

Preferably, the content of free amino groups of the polyamino acid after crosslinking of the polyamino acid, in particular with citric acid, is between 25 and less than 50%, in particular between 30 and 45%, preferably between 35 and 43%, based on the original total amount of amino groups of the amino acid monomers, preferably lysine monomers, used for the preparation of the polyamino acid. Preferably, a polylysine, in particular poly-ε-lysine, crosslinked with 5 mol % of citric acid with respect to the lysine monomers employed, has a content of free amino groups of about 43% and a polylysine, in particular poly-ε-lysine, crosslinked with 10 mol % of citric acid with respect to the lysine monomers employed, has a content of free amino groups of about 35%, based on the original total amount of amino groups of the lysine monomers used for the preparation of the polyamino acid.

In a further preferred embodiment, the content of free amino groups of the polyamino acid after the amphiphilic modification of the crosslinked polyamino acid is between 15 and 35%, in particular between 25 and 35%, preferably about 30%, based on the original total amount of amino groups of the amino acid monomers, preferably lysine monomers, used for the preparation of the polyamino acid. In a particularly preferred embodiment, a polylysine, in particular poly-ε-lysine, crosslinked with 5 mol % of citric acid with respect to the lysine monomers employed has, after the amphiphilic modification, a content of free amino groups of about 32% and a polylysine, in particular poly-ε-lysine, crosslinked with 10 mol % of citric acid with respect to the lysine monomers employed has, after the amphiphilic modification, a content of free amino groups of about 26%, based on the original total amount of amino groups of the lysine monomers used for the preparation of the polyamino acid.

In the case of the metal nanoparticles, according to the invention these can be gold, silver, copper or zinc nanoparticles, silver nanoparticles being particularly preferred. Advantageously, the metal nanoparticles have a diameter of 0.5 to 20 nm, in particular 1 to 20 nm, preferably 1 to 14 nm.

Preferably, nanosilver particles which are stabilized by polyamino acids, in particular polylysine, preferably poly-ε-lysine, uncrosslinked and amphiphilically modified with a mixture of palmitoyl and stearoyl chloride, have a diameter of about 6 nm, in particular after reduction with ascorbic acid. In some cases, however, it can be preferable for the nanosilver particles to have a smaller diameter, in particular of about 4 nm. This is possible, for example, by reduction with the reductant $LiBHEt_3$.

According to another preferred embodiment, nanosilver particles which are stabilized by crosslinked polyamino acids, in particular polylysine, preferably poly-ε-lysine, in particular crosslinked by citric acid, and amphiphilically modified with a mixture of palmitoyl and stearoyl chloride, have a diameter of about 10 nm (5 mol % of citric acid with respect to the lysine monomers employed) or about 8 nm (10 mol % of citric acid with respect to the lysine monomers employed). This can be achieved, for example, by reduction with ascorbic acid.

In some cases, it can be desirable for the metal nanoparticles, in particular silver nanoparticles, of the complex material to have a diameter in the range from 2.5 to 3.5 nm. This can be achieved, for example, by use of polylysine, preferably of poly-ε-lysine. The polylysine is preferably crosslinked with citric acid and in particular amphiphilically modified with a mixture of palmitoyl and stearoyl chloride. Thus, the metal nanoparticles in the case of stabilization by polylysine which is crosslinked with 5 mol % of citric acid with respect to the lysine monomers employed can have a diameter of about 3.1 nm. In the case of the use of polylysine which is crosslinked with 10 mol % of citric acid with respect to the lysine monomers employed, the metal nanoparticles can have a diameter of about 2.7 nm.

According to the invention, it can furthermore be provided that the medicotechnical product is a temporary or permanent implant for the human or animal body. Here, the antimicrobially finished implants are preferably joint implants, stents, screws, pins and plates. The implants can consist of metals or metal alloys. Possible further materials for the implants are, in particular, plastics. The implants can be used, for example, for the repair of fractures. The implants can furthermore be gauzes, preferably hernia gauzes. Possible further preferred implants are, in particular, vascular prostheses, membranes and films, for example for adhesion prophylaxis. According to the invention, it is furthermore preferred for the implants to be incontinence belts and generally textile implants. Suitable textile implants are, in particular, fabric, knitted and crocheted fabrics, noncrimp fabrics and nonwovens. The biocidal finish of these implants makes it possible also to introduce these into acutely infected or infection-endangered regions of the body, since the implants themselves have an antimicrobial action due to the finish and in this way contribute to a decrease in a present or potential infection.

In another embodiment, the medicotechnical products are medical instruments, in particular surgical scissors, forceps and clamps and also catheters or probes and other instruments, in particular for minimally invasive interventions. In this connection, the already mentioned adhesive connection of the antimicrobial finish to the surface of the medicotechnical product is particularly advantageous, since the medical instruments just described, for example, are exposed to particularly high mechanical stress, in particular due to rubbing and wiping. The adhesion of the antimicrobial finish to the product surface is in particular caused by lipophilic interactions, preferably van der Waals forces, of the long-chain aliphatic radicals of the substance, in particular pointing away from the metal nanoparticles, with the product surface.

The medicotechnical products according to the present invention can furthermore be products such as, for example, drainage tubes, suture materials or wound coverings. The material of the medicotechnical product, according to a further preferred embodiment, is a metal or a metal alloy, in particular titanium, stainless steel, magnesium, tantalum or an alloy thereof, magnesium and/or tantalum being particularly preferred because of their biocompatibility and resorbability.

In a further embodiment, the material of the medicotechnical product is a nonresorbable or an at least partially resorbable polymer. Thus the non-resorbable polymer can be a polyolefin, in particular polyethylene and/or polypropylene, a polyester, in particular polyethylene terephthalate and/or polybutylene terephthalate, a polyamide, in particular polyamide-6 or polyamide-6,6, or a natural fiber, in particular silk or linen. Preferably, the at least partially resorbable polymer is a completely resorbable polymer. The resorbable polymer can in particular be a polymer based on the monomers lactide, glycolide, trimethylene carbonate, para-dioxanone and/or ε-caprolactone, preferably in the form of a co- and/or terpolymer. According to a further embodiment, a medicotechnical product whose material is not resorbable can be coated with an at least partially resorbable, preferably completely resorbable, polymer, in particular with one of the polymers just listed, in order thus to influence or to regulate the access time of fluids, in particular of body fluids, to the antimicrobial finish.

In a further embodiment the material of the medicotechnical product is a ceramic material. Advantageously, it can be a resorbable ceramic material, in particular hydroxyapatite or tricalcium phosphate.

According to a further embodiment, the product has pores, preferably interconnecting pores. This can be particularly advantageous, since in this way an enlarged surface area is available for the antimicrobial finish. Thus a greater quantity of the biocidal or antimicrobial complex material can be applied to, and, in the case of an interconnecting pore system, also within the product to be finished.

The product is advantageously sterilizable and is in particular present in sterilized form. Suitable sterilization methods are all methods known to the person skilled in the art, in particular irradiation, steam sterilization, ethylene oxide fumigation and plasma sterilization, which preferably do not adversely affect the chemical structure and/or the antimicrobial properties of the complex material, which in particular is present in the form of a core-shell structure. In the state used, the medicotechnical product according to the invention is preferably present in sterile form.

The subject of the invention moreover relates to a process for the preparation of a medicotechnical product, the complex material, in particular in the form of a solution, being applied to the unfinished product from the outside. In the solution, the metal nanoparticles, in particular silver nanoparticles, are preferably present in stabilized form according to one of the preceding embodiments. The preparation of a solution of this type is preferably carried out starting from amphiphilically modified and in particular crosslinked polyamino acids. The core-shell polymers prepared in this way are dissolved in an organic solvent and loaded with the corresponding metal ion by addition of a metal salt. The solution prepared in this way contains metal ions stabilized by amphiphilically modified and in particular crosslinked polyamino acids and is suitable in particular for the antimicrobial finishing of medicotechnical products, in particular for the finishing of the medicotechnical products already mentioned. Preferably, the metal ions of the solution stabilized in this way are, however, reduced in the presence of a suitable reductant, in particular vitamin C, sodium borohydride, $LiHBEt_3$ or an aldehyde, to give elementary metal nanoparticles. In the case of the use of $LiHBEt_3$ (Li: lithium, H: hydrogen, B: boron and Et: ethyl) as a reductant, lithium/boron species derived therefrom on account of the oxophilicity of the boron can lead to crosslinking and thus to aggregation of the amphiphilically modified and, in particular, crosslinked polyamino acids. Therefore and in particular because of its biocompatibility, the use of vitamin C as a reductant is particularly preferred. As organic solvents, various alcohols, in particular isopropanol or propanol, or aromatic solvents, for example toluene or xylene, and mixtures thereof can be used.

Furthermore, it can be preferential to apply the antimicrobial complex material to the product to be finished as a solid, for example by sputtering, or in the form of a melt or of an aerosol.

Preferably, the antimicrobial complex material is applied to the surface of the unfinished product in an immersion process. Furthermore, the antimicrobial complex material can be put into and/or onto the unfinished product by swelling. For the antimicrobial finishing of, for example, suture materials, gauzes or belts, it can be preferential to apply the biocidal complex material to the unfinished product from the outside in the pull-through process. Furthermore, the biocidal complex material can be applied to the unfinished product by pouring, spreading, stamping and spraying techniques known to the person skilled in the art, in particular pressing, rolling or applying with a doctor blade.

According to a further embodiment, an at least partially resorbable, preferably completely resorbable, polymer, in particular in the form of a solution, is additionally applied to the surface of the product. Thus, it can be preferential for the product according to the invention to be provided in a second coating process with a second layer of a resorbable polymer, in particular of a polyester, polyurethane or silicone, after a superficial coating with the antimicrobial complex material. As a second layer, a resorbable co- and/or terpolymer, in particular based on lactide, glycolide, trimethylene carbonate, polybutyrate, para-dioxanone and/or $\epsilon$-caprolactone, is preferably applied.

As solvents, alcohols, aliphatic esters, ketones or aromatic solvents can be employed, ethyl acetate being particularly preferred. It is furthermore possible for the resorbable polymer to be applied to the product after a surface treatment of the medicotechnical product, in particular after plasma activation.

Alternatively to this, the at least partially resorbable, preferably completely resorbable, polymer and the antimicrobial complex material can be applied together to the medicotechnical product to be finished in a coating process. This is particularly advantageous, since a single coating process is more economical and thus more cost-effective.

Furthermore, it is possible for a ceramic and/or metallic coating, in particular according to one of the two last-described embodiments, to be applied to the product to be finished.

The invention furthermore relates to a process for the preparation of a medicotechnical product, the complex material, in particular in the form of a solution, being added to the material of the product during its preparation additionally or alternatively to the prior embodiments or being intercalated therein by swelling after preparation of the product. By addition to the material of the product, a uniform distribution of the antimicrobial complex material within the medicotechnical product and on its surface or at least in layers close to the product surface can be achieved. With respect to further details, in particular with respect to the solution and to alternative forms of addition of the antimicrobial complex material to the material of the medicotechnical product, in particular as a solid or in the form of a melt or of an aerosol, reference is made to the above description.

In a further advantageous embodiment, the antimicrobial complex material is mixed with the product material and subsequently shaped to give the desired product, in particular extruded, spun, pressed, rolled, poured or blown. Particularly preferably, a mixture of polymer and antimicrobial complex material is spun to give a filamentous material, which according to the type of polymer used can be woven or knitted to give resorbable or to give nonresorbable suture material or to give a textile product.

The present invention furthermore relates to a process for the preparation of at least one polyamino acid, in particular for the preparation of the product according to the invention, by polymerization of at least trifunctional amino acids in the liquid phase, the amino acids being activated for the polymerization and polymerized without use of protective groups.

In one embodiment of the process according to the invention, organic solvents or organic solvent mixtures are used for making available the liquid phase. Advantageously, the polymerization of the amino acids is performed in at least one solvent selected from the group comprising dimethyl sulfoxide (DMSO), dimethylformamide (DMF), dichloromethane, tetrahydrofuran (THF) and ethyl acetate.

In a preferred embodiment of the process according to the invention, the amino acids are activated by at least one substance, preferably an organic substance. Particularly advantageously, a nitrogen-containing compound is used as the substance. Preferably, the amino acids are converted by reaction with the substance into particularly reactive intermediates, in particular into active esters, and thus activated. The amino acids activated in this way can react with nucleophilic groups, in particular with amino groups, of other amino acids. The polymerization of the amino acids to the polyamino acid can thereby be performed under particularly mild reaction conditions, in particular at room temperature.

In one particular embodiment of the process according to the invention, the amino acids are activated by at least one substance from the group comprising carbodiimides, N-hydroxysuccinimide (NHS), 1-hydroxybenzotriazole (HOBT) and derivatives derived therefrom. Furthermore, the amino acids can be activated by reaction with pentachlorophenol and/or pentafluorophenol. As carbodiimides, in particular 1-ethyl-3-(3-dimethylaminopropyl)carbodiimide (EDC) or dicyclohexylcarbodiimide (DCC) can be used. The use of EDC can be preferable, in particular because of its good water solubility. For instance, the isourea derivative formed after successful polymerization and derived from EDC can be removed from the reaction mixture by simple purification steps, in particular by aqueous extraction. In another embodiment, it can be useful to activate the amino acids for the polymerization by DCC.

In some cases, the activation potential of carbodiimides, in particular of DCC, is not adequate for satisfactory polymerization, since, for example, the intermediates activated by carbodiimides can in particular be deactivated by secondary reactions. These undesired secondary reactions can in particular be rearrangement reactions, by means of which the activated intermediates, in particular active esters, are converted to deactivated products, in particular amide compounds, before they can polymerize to the desired polyamino acid. In such cases, it can be useful according to the invention to activate the amino acids by carbodiimides, in particular DCC, and a further substance. Preferably, the further substance reacts with the activated intermediates formed from the carbodiimides and the amino acids with formation of novel, preferably more reactive, intermediates, in particular with formation of active esters. The more active intermediates prepared in this way react particularly rapidly with the amino groups of the amino acids employed for the polymerization.

In this way, a deactivation of active intermediates can be avoided particularly advantageously. In particular, the preparation of a polyamino acid, for example of a polyamino acid having a desired DP (degree of polymerization), is thus possible.

In a particularly preferred embodiment of the process according to the invention, the amino acids are activated by dicyclohexylcarbodiimide (DCC) and N-hydroxysuccinimide (NHS).

In another preferred embodiment of the process according to the invention, the amino acids are activated by dicyclohexylcarbodiimide (DCC) and 1-hydroxybenzotriazole (HOBT).

Furthermore, the amino acids can be activated by thionyl chloride ($SOCl_2$) in DMF as a solvent, the activation preferably being performed by means of a DMF-catalyzed reaction with thionyl chloride ($SOCl_2$).

Furthermore, the amino acids can be activated by heating the liquid phase. Particularly advantageously, a condensation reaction between the carboxyl and amino groups of the amino acids with removal of water and formation of amide bonds is performed by heating. The activation is in particular carried out at a temperature (reaction temperature) between 100 and 150° C., in particular between 110 and 140° C. The activation and linkage of the amino acid monomers is in particular performed for a period of 8 to 96 hours, preferably for about 96 hours. Advantageously, the reaction procedure can be carried out at different temperatures, in particular at two different temperatures. Particularly advantageously, the polymerization can be carried out at temperatures of about 140° C. and about 110° C. Preferably, the reaction mixture is first brought to a temperature of about 140° C. and kept at this temperature for about 48 hours. Subsequently, the reaction mixture is preferably cooled to a temperature of about 110° C. and kept at this temperature for about a further 48 hours. Preferably, concentrations of between 2 and 20 mol/l, in particular between 5 and 17 mol/l, preferably a concentration of about 15 mol/l, are used as initial concentrations for the amino acids.

Furthermore, it can be preferential according to the invention to activate the amino acids by silylation, in particular by reaction with hexamethyldisilazane (HMDS). By means of the silylation, silylated amino acids result, the heteroatoms of the amino acids being at least partially covalently bonded to silyl groups, in particular to trimethylsilyl groups. The amino acids activated in this way can be polymerized to the polyamino acid.

The polyamino acids prepared can be purified, in particular, by filtration and/or dialysis. In the case of cationic, in particular polycationic, polyamino acids, purification is particularly advantageously carried out with the aid of the "CMC (carboxymethyl-cellulose) method". In the CMC method, the polyamino acids preferably form stable insoluble aggregates with the polyanionic carboxymethylcellulose soluble in an aqueous-basic environment. These aggregates can be separated off from the aqueous environment by filtration and in particular often washed if desired. All impurities can thus be eliminated. The release of the polyamino acids from the insoluble aggregates is preferably carried out by acidifying in an aqueous environment, since in this way the protonated carboxymethylcellulose (CMC) remains insoluble and the polyamino acids go into solution. Optionally, when using the CMC method, the dialysis step for the purification of the polyamino acids can be dispensed with. By suitable choice of the parameters, in particular of the pH, the concentration, the rate of addition and the nature of the carboxymethylcellulose used, it can be achieved that individual amino acids oligomers of the polyamino acid form no aggregates with CMC and can advantageously be removed by washing steps.

In a further preferred embodiment of the process according to the invention, the polyamino acid is modified amphiphilically in a liquid phase, in particular in the presence of bases. For the preparation of the liquid phase, in particular organic solvents or mixtures, in particular THF, and water are suitable. As bases, amines, in particular triethylamine, are preferably used. According to the invention, it is particularly preferred that water-soluble bases, in particular alkali metal hydroxide solutions, preferably sodium hydroxide solution, are used for the amphiphilic modification of the polyamino acid. Preferably, the polyamino acid is dissolved in a liquid phase, preferably in an aqueous phase. In a preferred embodiment of the process according to the invention, a solution of the substance intended for the amphiphilic modification is added to the solution of the polyamino acid to be modified. Preferably, the substance is dissolved in at least one organic solvent, in particular THF. Furthermore, a solution, in particular an aqueous solution, of the base is added to the solution of the polyamino acid to be modified. In a particularly preferred embodiment of the process according to the invention, the solution of the substance intended for the amphiphilic modification and the solution of the base is in each case added simultaneously to the solution of the polyamino acid. Particularly advantageously, the addition can be carried out by dropwise addition. According to the invention, it is furthermore particularly preferred for the substance used for the amphiphilic modification of the polyamino acid to be at least one fatty acid, preferably palmitic and/or stearic acid, or a fatty acid derivative, preferably palmitoyl and/or stearoyl chloride. With respect to further details, reference is made to the previous description.

Preferably, branched, in particular hyperbranched, polyamino acids, in particular homopolyamino acids, preferably poly-ε-lysine, are prepared with the aid of the process according to the invention described above. With respect to further details, reference is made to the previous description.

Furthermore, the invention comprises the use of a complex material of metal nanoparticles and macromolecules, the macromolecules being formed at least partially from a polyamino acid and in particular each metal nanoparticle being surrounded in a shell-like manner, as a biocide in a medicotechnical product. With respect to further features and details, reference is made to the previous description.

On account of the molecular structure and the construction of its finish, the product according to the invention has biocompatible, in particular tissue-compatible, properties and simultaneously extremely effective antimicrobial and/or biocidal properties. The composition of the complex material of endogenous substances or of substances which are synthesized from endogenous compounds, and/or of at least essentially body-compatible substances guarantees the biocompatibility of the antimicrobially finished product just mentioned.

The antimicrobial properties of the finish are based both on the biocidal action of the metal nanoparticles, in particular silver nanoparticles, and on the biocidal action of the polyamino acid, in particular poly-ε-lysine. The bringing together of these antimicrobially active substances in the form of a complex material brings about its high efficacy against, in particular, harmful microorganisms or germs. Particularly advantageously, by means of a core-shell structure of the complex material, on the one hand the stabilization of the metal nanoparticles can be brought about and thus a deposition and uncontrollable accumulation of the metal in the body can be prevented. On the other hand, the hydrophobic shell of the core-shell structure brings about the adhesion of the finish, in particular to the product surface. In this way, the risk of an uncontrollable or alternatively a continuous release of the metal into the environment, in particular into the surrounding body tissue, can be reduced. Thus, side effects possibly occurring in this connection can be diminished or essentially prevented.

Further features of the invention are clear from the following description of preferred embodiments with the aid of examples. Here, the individual features of the invention can be realized alone or in combination with one another. The embodiments described serve only for illustration and for better comprehension of the invention and are in no manner to be understood as restrictive.

EXAMPLE 1

Preparation of ε-poly-L-lysine 0.627 g of 1-ethyl-3-[3-(dimethylamino)propyl]-carbodiimide hydrochloride was added at room temperature in five portions to a solution of 0.200 g of L-lysine hydrochloride in 4 ml of water (dist.), the reaction solution being stirred for 24 hours between two additions. After the end of polymerization, the reaction mixture was dialyzed against water (dialysis membrane having a cut-off of 2000 g/mol) and the polypeptide was subsequently obtained (yield: 0.016 g [9%]).

EXAMPLE 2

Polymerization of L-lysine by addition of DCC 566 mmg (2.74 mmol, 2.0 equivalents) of dicyclohexylcarbodiimide were added to a stirred colorless suspension of 200 mg of L-lysine (1.37 mmol, 1.0 equivalent) in 5 ml of ethyl acetate. The colorless suspension (not milky) was stirred at room temperature for 4 days and subsequently concentrated to dryness by removal of the solvent. The resulting solid was treated with 20 ml of water and the resulting colorless suspension was centrifuged (10 minutes at 4000 revolutions per minute). The colorless solid separated off was washed twice with 10 ml of water each time. The combined aqueous clear phases were concentrated to about 10 ml of solution, turbidity occurring. The resulting suspension was filtered and the filtrate was dialyzed against water (MWCO 2000). About 1 mg of colorless polymer was obtained from the dialysis.

EXAMPLE 3

Polymerization of L-lysine by addition of DCC/NHS 566 mg (2.74 mmol, 2.0 equivalents) of dicyclohexylcarbodiimide and 316 mg (2.74 mmol, 2.0 equivalents) of N-hydroxysuccinimide (NHS) were added to a stirred colorless suspension of 200 mg of L-lysine (1.37 mmol, 1.0 equivalent) in 5 ml of ethyl acetate. The milky suspension was stirred at room temperature for 4 days and subsequently concentrated to dryness by removal of the solvent. The resulting solid was treated with 20 ml of water and the resulting colorless suspension was centrifuged (10 minutes at 4000 revolutions per minute). The colorless solid separated off was washed twice with 10 ml of water each time. The combined aqueous clear phases were concentrated to about 10 ml, turbidity occurring. The resulting suspension was filtered and the filtrate was dialyzed against water (MWCO 2000). 55 mg of colorless poly-L-lysine (0.43 mmol of lysine units, yield: 33%) were obtained from the dialysis.

EXAMPLE 4

Silylation of L-lysine using hexamethyldisilazane (HMDS)

9.14 g of L-lysine hydrochloride (0.05 mol, 1.0 equivalent) were suspended in 53 ml of hexamethyldisilazane (41.02 g, 0.254 mmol, 5.1 equivalents) and the suspension was heated to 130° C. After 8 hours, a yellow solution was obtained. After 24 hours, the solution was dark-brown. Residual hexamethyldisilazane was removed in vacuum (63° C., 20 mbar) and a dark-brown oily mass was obtained. By means of distillation (90° C., 0.1 mbar), 5.68 g of colorless oil of silylated L-lysine were obtained. Using a degree of silylation of 1.9 per lysine molecule, a yield of 40% was calculated with respect to the L-lysine employed.

EXAMPLE 5

Polymerization of the silylated L-lysine 2.860 mg of silylated L-lysine (about 0.012 mol lysine content and about 0.023 mol, 1.0 equivalent, trimethylsilyl content) were heated to 80° C. under reflux and 1.0 ml of isopropanol (0.785 g, 0.013 mol, 0.6 equivalent) was slowly added dropwise thereto. An orange solid in a pale yellow liquid was slowly formed. After 8 hours, the mixture was cooled to room temperature and a further 1.4 ml of isopropanol were added. After one hour, 2 ml of water were added and the entire solvent and the resulting hydroxytrimethylsilane were removed in vacuum. The residue was dissolved in water and dialyzed against water (MWCO 2000). 60 mg of yellowish polymer (about 4% yield) were obtained from the dialysis.

EXAMPLE 6

Polycondensation 7.422 g of L-lysine.$H_2O$ (0.045 mol) were dissolved in 5.0 ml of water in an ultrasonic bath. Subsequently, sufficient water was removed on a rotary evaporator until turbidity occurred, which changed in the air to a clear viscous solution. By differential weighing, it followed that 3.0 ml of water remained as solvent. The aqueous L-lysine solution was heated under reflux to 160° C. (oil bath temperature) and stirred for 2 days. Subsequently, the temperature was brought down to 120° C. and the mixture was stirred for a further 2 days. A gentle stream of nitrogen was regularly passed through the apparatus for a few minutes during the reaction in order to remove water. After reaction was complete, the mixture was cooled to room temperature and the very viscous orange mass was dissolved in water and subsequently dialyzed against water (MWCO 2000). 2.278 g of polymer were obtained from the dialysis (yield: about 37%).

EXAMPLE 7

Modification of ε-poly-L-lysine

61 μl of $NEt_3$ (triethylamine) were added at room temperature to a suspension of 12 mg of dried ε-poly-L-lysine in 3 ml of i-propanol (isopropanol). The mixture was stirred for 30 minutes. Subsequently, a solution of 142 μl of the mixture of palmitoyl and stearoyl chloride (40:60 mixture, % by weight) were slowly added dropwise in 1 ml of i-propanol. Here, a vacuum (750-800 mbar) was applied for a few seconds a number of times in order to remove aerosol formed. After addition of the acid chloride was complete, the reaction solution was stirred at room temperature for a further 24 hours. Subsequently, 61 µl of NEt₃ were again added and the mixture was stirred for 12 hours. The ϵ-poly-L-lysine modified with fatty acid (degree of modification 27%, corresponds to the content of free amino groups of the polylysine which have reacted with the mixture of palmitoyl and stearoyl chloride) was obtained from the dialysis (dialysis membrane having a cut-off of 2000 mg/mol) against i-propanol.

EXAMPLE 8

Modification of poly-L-lysine 0.500 g of the polylysine synthesized according to Example 6 (about 3.900 mmol, 1.0 equivalent) was dissolved in 20 ml of water. With stirring, a solution of 1.450 ml of acid chloride (1.313 mg, 4.500 mmol, 1.2 equivalents) in 6 ml of THF and simultaneously a solution of 0.180 g of sodium hydroxide solution (4.500 mmol, 1.2 equivalents) in 2 ml of water were added dropwise at room temperature. The solution became turbid even after addition of small amounts of acid chloride solution. After addition was complete, a milky, thick suspension was obtained, which was stirred overnight at room temperature. The suspension was centrifuged and subsequently filtered and the colorless solid was washed twice with 30 ml of water each time and subsequently dried in vacuum. Subsequently, i-propanol was added to the solid and the yellowish suspension was dialyzed against i-propanol (MWCO 2000). 873 mg of polymer were obtained from the dialysis, i.e. on complete reaction of a yield of 60% of the poly-L-lysine employed—now amphiphilically modified.

EXAMPLE 9

Crosslinking of ϵ-poly-L-lysine by citric acid

First, a polymerization of 0.200 g of L-lysine hydrochloride (1.00 equivalent) was carried out according to Example 1. Subsequently, after 24 hours of the last EDC addition, a freshly prepared solution of 0.011 g of citric acid (0.055 mmol, 0.05 equivalent) and 0.032 g of EDC.HCL (0.167 mmol, 0.15 equivalent) in 1 ml of water was added. For higher crosslinkage, 0.021 g of citric acid (0.110 mmol, 0.10 equivalent) and 0.064 g of EDC.HCL (0.334 mmol, 0.30 equivalent) were employed in the same procedure and same mixture.

EXAMPLE 10

Loading of the Polymer Article with Silver(I) Nitrate and Reduction 10 mg of modified ϵ-poly-L-lysine were dissolved in 7.6 ml of toluene under a nitrogen atmosphere and 5.7 mg of AgNO₃ were added in three portions (stirring time of 24 hours after each addition). A clear and stable silver(I) polymer-toluene solution was obtained. 0.1 ml of the silver(I) polymer-toluene solution (contents: 0.13 mg of polymer, 0.05 mg of AgNO₃) was diluted with 2 ml of i-propanol and treated with 0.03 ml of a 0.02 M L-ascorbic acid solution (in i-propanol). The solution turned intensely yellow. Alternatively, 0.1 ml of the silver(I) polymer-toluene solution (contents: 0.13 mg of polymer, 0.05 mg of AgNO₃) can be diluted with 2 ml of i-propanol and treated with 0.06 ml of a diluted 0.01 M (M: molarity) Li[HBEt₃] solution (in THF). The solution likewise turns intensely yellow.

EXAMPLE 11

Preparation of Films on Glass Slides

For the preparation of a film, a silver(0) polymer solution was applied to a marked area of about 1 cm² of a glass slide using a pipette. The slide was placed on a hotplate and the solvent was evaporated. In this process, the solution on the glass, which was becoming more and more concentrated, was stirred with the pipette such that a film was formed in the marked zone.

EXAMPLE 12

Bacterial Tests

For the bacterial tests, films about 1 cm² in size were prepared on glass slides: 4 µg of silver in 40 µg of polymer or 10 µg of silver in 100 µg of polymer. For the preparation of the bacterial cells, 50 ml of a sterile standard culture medium from Merck were inoculated with 100 µl of suspension of *Staphylococcus aureus* cells (about $10^{11}$ cells per ml) in PBS (phosphate-buffered saline, pH 7.0) and incubated for 6 hours at 37° C. with shaking. After centrifuging the bacterial suspension, the cells were washed twice with PBS (pH 7.0), then resuspended using PBS and diluted further with PBS to a concentration of $5 \times 10^8$ cells per ml. The cell concentration was checked by means of the absorption at 600 nm. The prepared films were washed for 2 minutes in PBS and sprayed with the bacterial suspension. Subsequently, the slides were placed in one petri dish each and 25 ml of growth agar (1.5% by weight agar in growth medium was heated to 100° C. for 5 minutes and rapidly cooled to 40° C.) were added. After this, the petri dishes were incubated at 37° C. The films with a minimum amount of silver of 10 µg per cm² prevented growth of the sprayed-on *Staphylococcus aureus* cells to more than 99%.

The invention claimed is:

1. A medicotechnical product having an antimicrobial finish of a complex material of metal nano-particles and macromolecules, the macromolecules being formed at least partially from a polyamino acid, wherein the polyamino acid is amphiphilically modified with a substance, wherein the substance is bonded to the polyamino acid by means of a crosslinking component.

2. The medicotechnical product as claimed in claim 1, wherein the finish is provided on at least one part of the surface of the product.

3. The medicotechnical product as claimed in claim 1, wherein the finish is provided in the interior of the product.

4. The medicotechnical product as claimed in claim 1, wherein each metal nanoparticle is surrounded in a shell-like manner by at least one polyamino acid.

5. The medicotechnical product as claimed in claim 1, wherein the polyamino acid is one of the groups consisting of homopolyamino acids and heteropolyamino acids.

6. The medicotechnical product as claimed in claim 1, wherein the polyamino acid consists of at least one of the groups consisting of naturally occurring and synthetic amino acids.

7. The medicotechnical product as claimed in claim 1, wherein the polyamino acid contains at least one amino acid of the group consisting of basic, acidic and sulfur-containing amino acids.

8. The medicotechnical product as claimed in claim 1, wherein the polyamino acid has a linear structure.

9. The medicotechnical product as claimed in claim 1, wherein the polyamino acid has a branched structure.

10. The medicotechnical product as claimed in claim 1, wherein the polyamino acid is polylysine.

11. The medicotechnical product as claimed in claim 10, wherein the polylysine has a degree of polymerization (DP) of 10 to 15.

12. The medicotechnical product as claimed in claim 10, wherein the polylysine has a molecular weight between 3000 and 6000 g/mol.

13. The medicotechnical product as claimed in claim 1, wherein the polyamino acid is amphiphilically modified with a substance having at least one aliphatic radical.

14. The medicotechnical product as claimed in claim 13, wherein the aliphatic radical has 6 to 22 carbon atoms.

15. The medicotechnical product as claimed in claim 13, wherein the substance is at least one biocompatible substance.

16. The medicotechnical product as claimed in claim 13, wherein the amphiphilic modification of the polyamino acid is based on covalent bonds.

17. The medicotechnical product as claimed in claim 13, wherein the content of free amino groups after the amphiphilic modification is between 0.5 and less than 50% based on the original total amount of amino groups of the amino acid monomers used for the preparation of the polyamino acid.

18. The medicotechnical product as claimed in claim 17, wherein the content of free amino groups after the amphiphilic modification of the crosslinked poly-amino acid is between 15 and 45% based on the original total amount of amino groups of the amino acid monomers used for the preparation of the polyamino acid.

19. The medicotechnical product as claimed in claim 1, wherein the metal nanoparticles are one of the groups consisting of gold, silver, copper and zinc nanoparticles.

20. The medicotechnical product as claimed in claim 1, wherein the metal nanoparticles have a diameter of 0.5 to 20 nm.

21. A process for the preparation of a medicotechnical product as claimed in claim 1, wherein the complex material is added by at least one manner consisting of the group of applying to the unfinished product from the outside and adding to the material of the product during its preparation.

22. A process for the preparation of the macromolecules of claim 1 by polymerizing of at least trifunctional amino acids in the liquid phase, wherein the amino acids are activated for the polymerization and polymerized without use of protective groups.

23. The process as claimed in claim 22, wherein the amino acids are activated by at least one organic substance.

24. The process as claimed in claim 22, wherein the amino acids are activated by at least one substance of the group consisting of carbodiimides, N-hydroxysuccinimide (NHS), 1-hydroxybenzotriazole (HOBT), pentafluorophenol, pentachlorophenol and derivatives derived therefrom.

25. The process as claimed in claim 22, wherein the amino acids are activated by dicyclohexylcarbodiimide (DCC) and N-hydroxysuccinimide (NHS).

26. The process as claimed in claim 22, wherein the amino acids are activated by dicyclohexylcarbodiimide (DCC) and 1-hydroxybenzotriazole (HOBT).

27. A biocide in a medicotechnical product in the form of a complex material of metal nanoparticles and macromolecules, the macro-molecules being formed at least partially from a polyamino acid as claimed in claim 1.

28. The mediotechnical product as claimed in claim 7, wherein the poly-amino acid contains at least one amino acid from the group consisting of cysteine, methionine, tryptophan, histidine, arginine, lysine, ornithine, aspartic acid, glutamic acid and their derivatives.

29. A biocide in a mediotechnical product as claimed in claim 15, wherein the substance is a fatty acid or a fatty acid derivative.

30. A biocide in a mediotechnical product as claimed in claim 19, wherein the metal nanoparticles are silver nanoparticles.

31. A process as claimed in claim 21, wherein the complex material is added in the form of a solution.

32. A biocide as claimed in claim 27, in the form of a mediotechnical product of having an antimicrobial finish of a complex material of metal nano-particles and macromolecules, the macromolecules being formed at least partially from a polyamino acid.

* * * * *